(12) United States Patent
Finnestad (10) Patent No.: US 8,727,166 B2
(45) Date of Patent: May 20, 2014

(54) DISPOSAL CONTAINER WITH LOCKING CLOSURE

(71) Applicant: Covidien LP, Mansfield, MA (US)

(72) Inventor: Mark Brian Finnestad, Franklin, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/716,383

(22) Filed: Dec. 17, 2012

(65) Prior Publication Data

US 2014/0008364 A1 Jan. 9, 2014

Related U.S. Application Data (63) Continuation of application No. 12/853,352, filed on Aug. 10, 2010, now Pat. No. 8,333,292.

(51) Int. Cl.
| | |
|---|---|
| *B65D 51/18* | (2006.01) |
| *B65F 1/16* | (2006.01) |
| *B65D 90/58* | (2006.01) |
| *B65F 1/14* | (2006.01) |

(52) U.S. Cl.
CPC .............. *B65D 51/18* (2013.01); *B65D 90/587* (2013.01); *B65D 2543/00537* (2013.01); *B65D 2543/00453* (2013.01); *B65F 1/1623* (2013.01)
USPC ....................................... 220/254.9; 220/812

(58) Field of Classification Search
CPC ......... B65F 1/1623; B65F 1/16; B65D 51/18; B65D 2543/00537; B65D 2543/00481; B65D 2543/00453; B65D 2543/00444; B65D 43/0216; B65D 43/0218; B65D 43/0214; B65D 43/12; B65D 90/587; B65D 90/58
USPC ............ 220/254.9, 254.1, 259.5, 256.1, 812, 220/811, 810, 345.1, 908, FOR. 184, 220/FOR. 183, 200, 790, 789, 780, 802, 220/801, 796
IPC ....................... B65D 51/18,51/00, 43/20, 43/14
See application file for complete search history.

(56) References Cited

U.S. PATENT DOCUMENTS 3,817,420 A * 6/1974 Heisler .......................... 220/790
4,340,140 A 7/1982 Wilcox et al.
(Continued)

OTHER PUBLICATIONS

Office action issued Apr. 5, 2012 in related U.S. Appl. No. 12/853,352 now issued as Patent No. 8,333,292—6 pgs.

(Continued)

*Primary Examiner* — Robert J Hicks
(74) *Attorney, Agent, or Firm* — Lisa E. Winsor, Esq.

(57) ABSTRACT

A lid for covering an interior of a medical waste receptacle base. The lid includes a cover having a generally circular opening. The opening including an upper rim surrounding an upper central axis and a lower rim surrounding a lower central axis that is non-co-linear with the upper central axis. The lid includes a generally circular closure sized for blocking the opening. The lid includes a guide extending along the cover. In the open position, the closure is at least partially out of alignment with the opening. In the closed position, a center axis of the closure is aligned with the upper central axis to block the opening. The closure is moveable from the closed position to a locked position in which the center axis of the closure is coincident with the lower central axis.

20 Claims, 12 Drawing Sheets

(56) References Cited

U.S. PATENT DOCUMENTS

| | | |
|---|---|---|
| 4,552,280 A | 11/1985 | Owen et al. |
| 4,657,139 A | 4/1987 | Hanifl |
| 4,972,950 A | 11/1990 | Shillington |
| 4,982,843 A | 1/1991 | Jones |
| 5,400,914 A | 3/1995 | Lin |
| 5,415,315 A | 5/1995 | Ramirez |
| 5,507,408 A | 4/1996 | Mosior et al. |
| 5,611,451 A | 3/1997 | Mosior et al. |
| 5,823,340 A | 10/1998 | Maihofer |
| 5,829,588 A | 11/1998 | Bloomfield |
| 6,024,217 A | 2/2000 | Ponsi et al. |
| 6,070,751 A | 6/2000 | Mejias |
| 6,585,114 B2 | 7/2003 | Kennedy et al. |
| 6,997,313 B2 | 2/2006 | Rigling |
| 8,333,292 B2 | 12/2012 | Finnestad |

OTHER PUBLICATIONS

Response filed Jun. 12, 2012 to Office Action dated Apr. 5, 2012 regarding related U.S. Appl. No. 12/853,352 now issued as Patent No. 8,333,292—8 pgs.

* cited by examiner

DISPOSAL CONTAINER WITH LOCKING CLOSURE

CROSS-REFERENCE TO RELATED APPLICATIONS

This application is a continuation application under 35 U.S.C §120 and claims the benefit of co-pending U.S. application Ser. No. 12/853,352 entitled DISPOSABLE CONTAINER WITH LOCKING CLOSURE, filed on Aug. 10, 2010, the entire contents of which are incorporated herein by reference in its entirety.

FIELD OF THE INVENTION

The present invention generally relates to waste disposal, and more particularly to a slidable lid of a waste disposal container having features to prevent inadvertent locking of the lid.

BACKGROUND

Healthcare providers and biomedical research facilities generate significant quantities of contaminated waste that is a potential source of disease and infection. Examples of such waste include syringes, needles, intravenous bags, catheters, wound care products, and other disposable patient care products. It is important that medical waste disposal containers limit access to their contents during use to prevent users from contacting the contaminated waste. Accordingly, there is a need for such containers.

SUMMARY

The present invention relates to a lid for covering an interior of a medical waste receptacle base. The lid comprises a cover sized and shaped for covering the interior of the medical waste receptacle base. The cover has a generally circular opening sized for passing medical waste into the interior of the base. The opening including a generally circular upper rim surrounding an upper central axis and a generally circular lower rim surrounding a lower central axis that is non-co-linear with said upper central axis. The lid further comprises a generally circular closure sized for blocking the opening. The lid further comprises a guide extending along the cover for guiding the closure between an open position and a closed position. In the open position, the closure is at least partially out of alignment with the opening to allow medical waste to pass through the opening for receipt in the interior of the base. In the closed position, a center axis of the closure is aligned with the upper central axis to block the opening to prevent medical waste from passing through the opening. The closure is moveable from the closed position to a locked position in which the center axis of the closure is coincident with the lower central axis.

This invention is further directed to a medical waste receptacle that comprises a base having an interior sized and shaped for receiving medical waste. The receptacle further comprises a cover sized and shaped for covering the interior of the base. The cover has a generally circular opening sized for passing medical waste into the interior of the base. The opening includes a generally circular upper rim surrounding an upper central axis and a generally circular lower rim surrounding a lower central axis that is non-co-linear with said upper central axis. The receptacle further comprises a generally circular closure sized for blocking the opening. The receptacle further comprises a guide extending along the cover for guiding the closure between an open position and a closed position. In the open position, the closure is at least partially out of alignment with the opening to allow medical waste to pass through the opening for receipt in the interior of the base. In the closed position, a center axis of the closure is aligned with the upper rim central axis to block the opening to prevent medical waste from passing through the opening. The closure is moveable from the closed position to a locked position in which the center axis of the closure is coincident with the lower rim central axis.

This invention is further directed to a lid for covering an interior of a medical waste receptacle base. The lid comprises a cover sized and shaped for covering the interior of the medical waste receptacle base. The cover has an opening sized for passing medical waste into the interior of the base. The lid further comprises a pair of parallel carriers extending toward opposite sides of the opening. The lid further comprises a closure sized and shaped for blocking the opening. The closure has a central portion and a peripheral flange surrounding the central portion. The closure also has a resiliently compliant lip extending from the flange and away from the interior of the medical waste receptacle base when the cover is covering the interior of the base. The lip engages the carriers to center the closure between the carriers for guiding the closure into alignment with the opening.

This invention is further directed to a medical waste receptacle that comprises a base having an interior sized and shaped for receiving medical waste. The receptacle further includes a cover sized and shaped for covering the interior of the medical waste receptacle base. The cover has an opening sized for passing medical waste into the interior of the base. The receptacle further includes a pair of parallel carriers extending toward opposite sides of the opening and a closure sized and shaped for blocking the opening. The closure has a central portion and a peripheral flange surrounding the central portion. The closure also has a resiliently compliant lip extending from the flange and away from the interior of the medical waste receptacle base when the cover is covering the interior of the base. The lip engages the carriers to center the closure between the carriers for guiding the closure into alignment with the opening.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
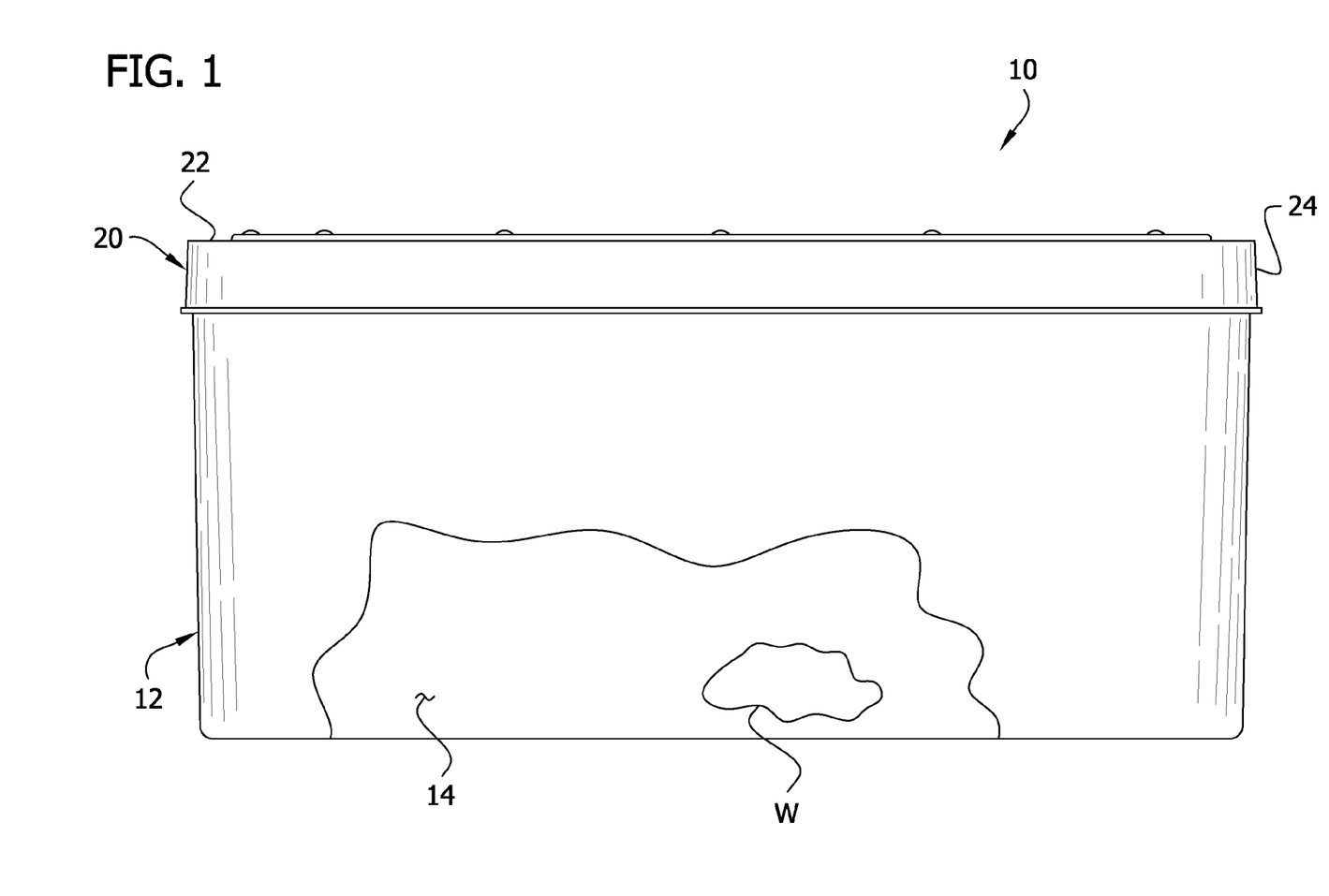
FIG. 1 is a side view of a medical waste receptacle of the present invention with portions broken away to show the interior of the medical waste receptacle.
Figure 2A:
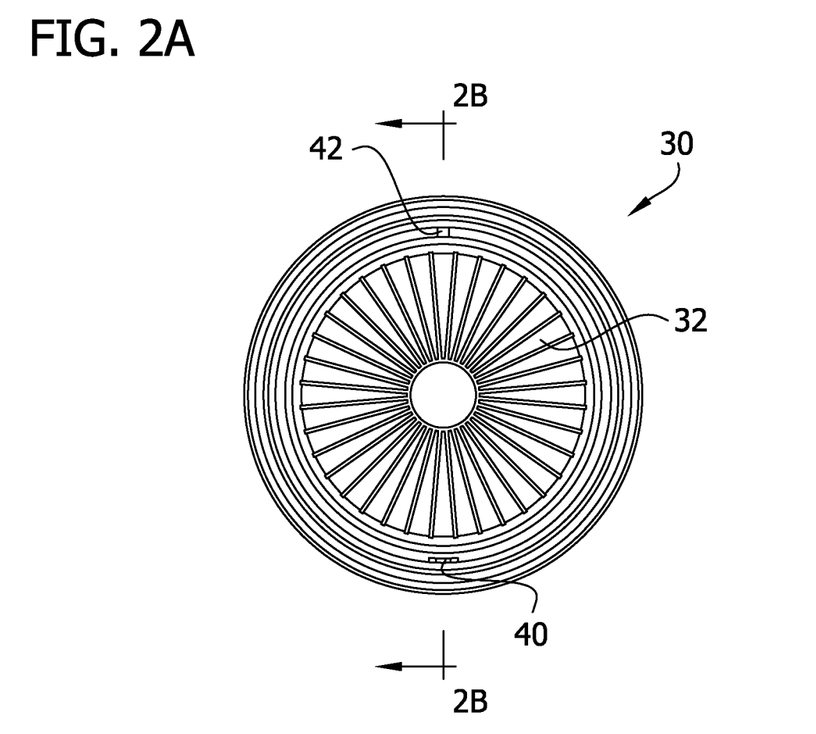
FIG. 2A is a top view of a closure of the present invention.
Figure 2B:
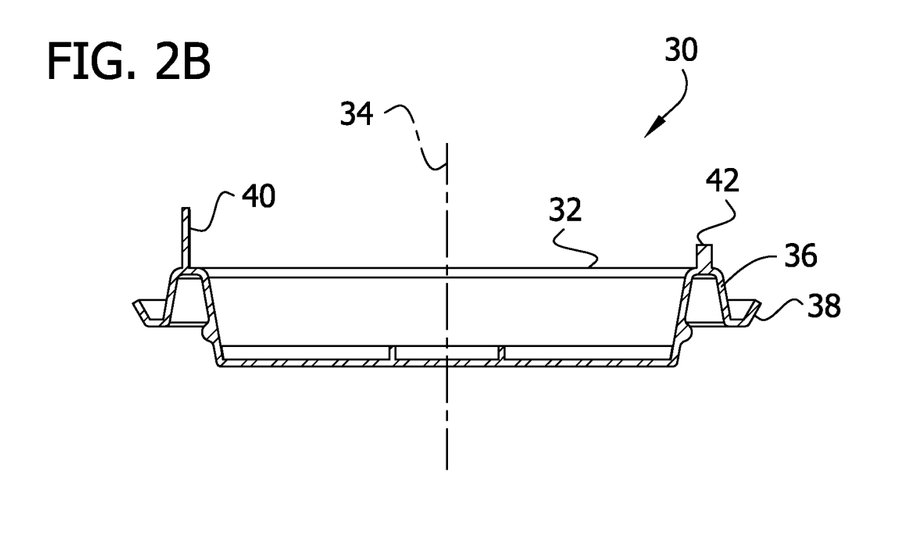
FIG. 2B is a vertical cross section of the closure of FIG. 2A taken in the plane 2B-2B.
Figure 3A:
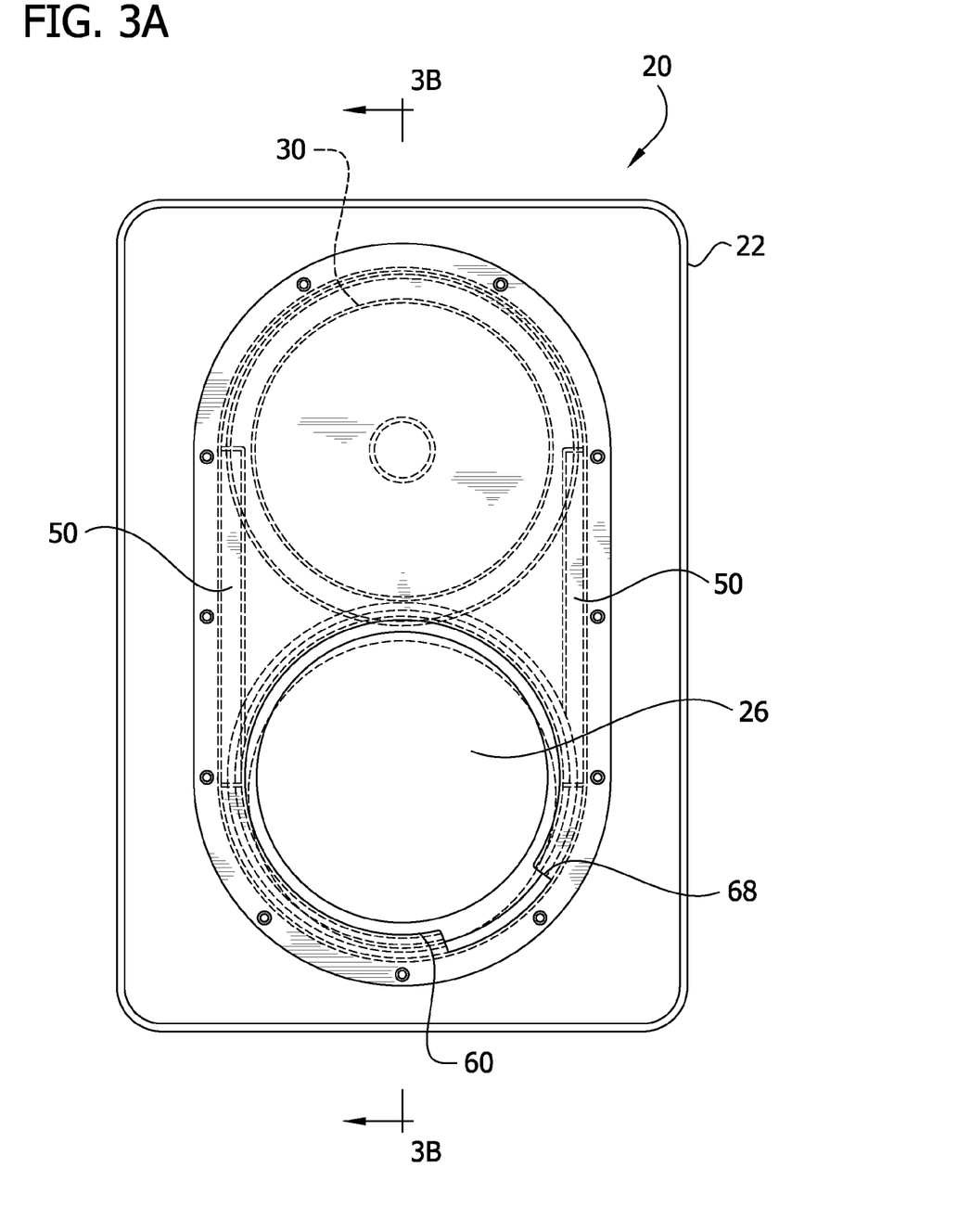
FIG. 3A is top view of a lid of the present invention with the closure in the open position.
Figure 3B:
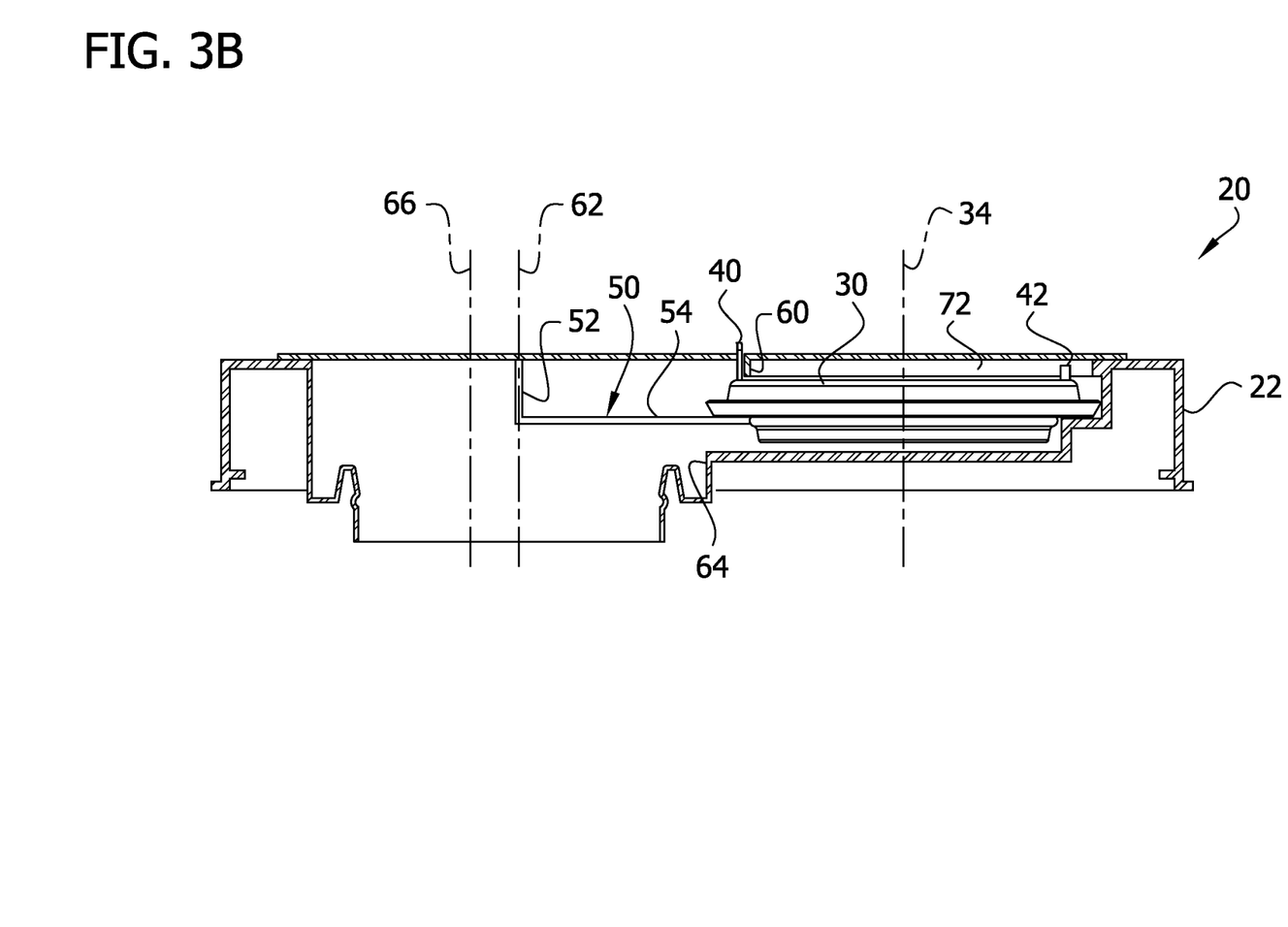
FIG. 3B is a vertical cross section of the lid of FIG. 3A taken in the plane 3B-3B.

Referring to FIGS. 1-3, a medical waste receptacle is generally designated by the reference number 10. The receptacle 10 includes a base 12 having an interior 14 sized and shaped for receiving medical waste W. Medical waste W is stored in the interior 14 of the base 12 until the receptacle 10 reaches a predetermined capacity and is deemed ready for disposal. The base 12 is conventional and will not be described in further detail. The receptacle also includes a lid 20 for covering the interior 14 of the base 12. The lid 20 includes a cover 22 sized and shaped for covering the interior of the medical waste receptacle base 12. The lid 20 has a conventionally shaped rim 24 extending around the cover 22 for attaching the lid 20 to the base 12. The lid 20 may be removably or permanently attached to base 12. In one embodiment, the lid 20 may be integrally formed with base 12. As best illustrated in FIG. 3A, the cover 22 has an opening 26 sized for passing medical waste W so a user can insert the waste into the interior 14 of the base without removing the lid 20 from the base 12.

Figure 4A:
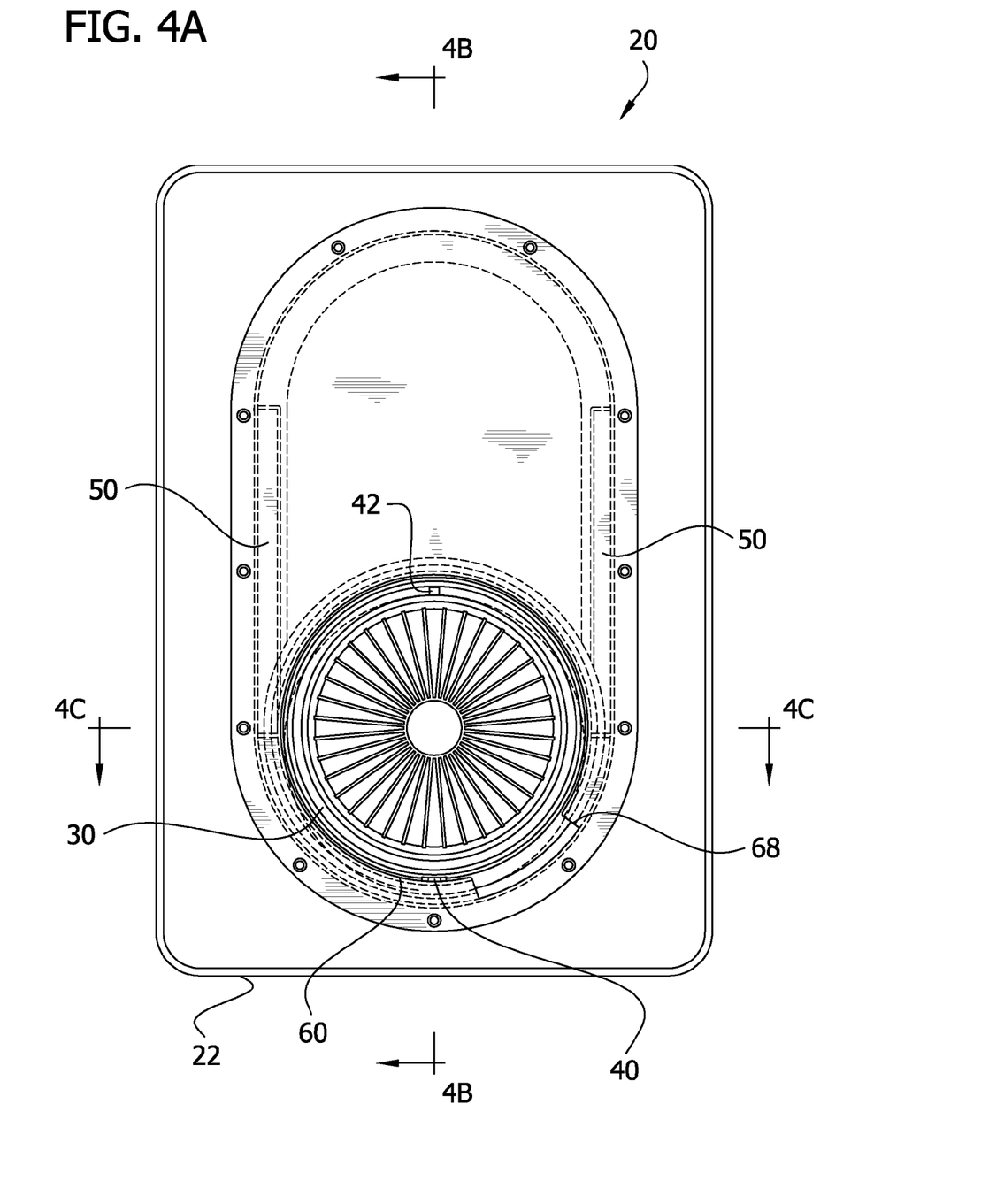
FIG. 4A is a top view of the lid with the closure in the closed position.
Figure 4B:
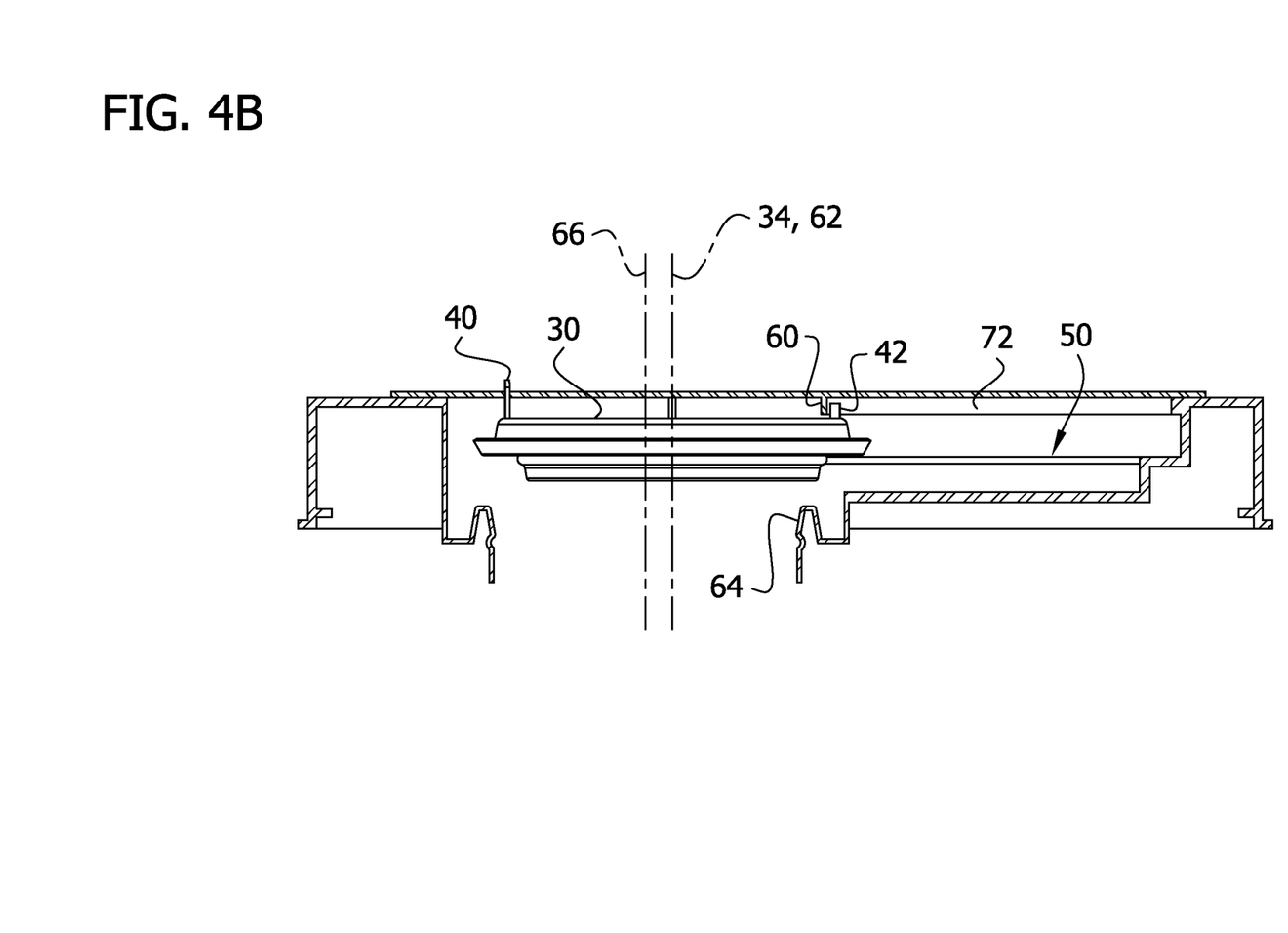
FIG. 4B is a vertical cross section of the lid of FIG. 4A taken in the plane 4B-4B.
Figure 4C:
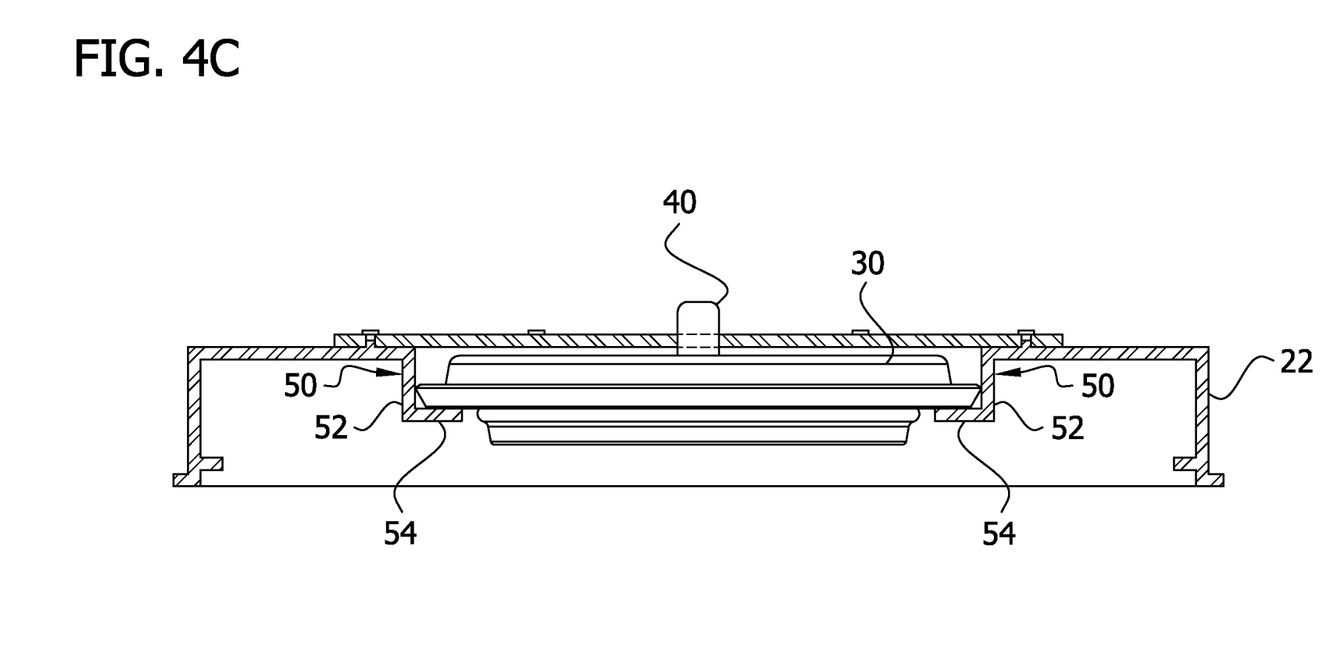
FIG. 4C is a horizontal cross section of the lid of FIG. 4B taken in the plane 4C-4C.
Figure 5A:
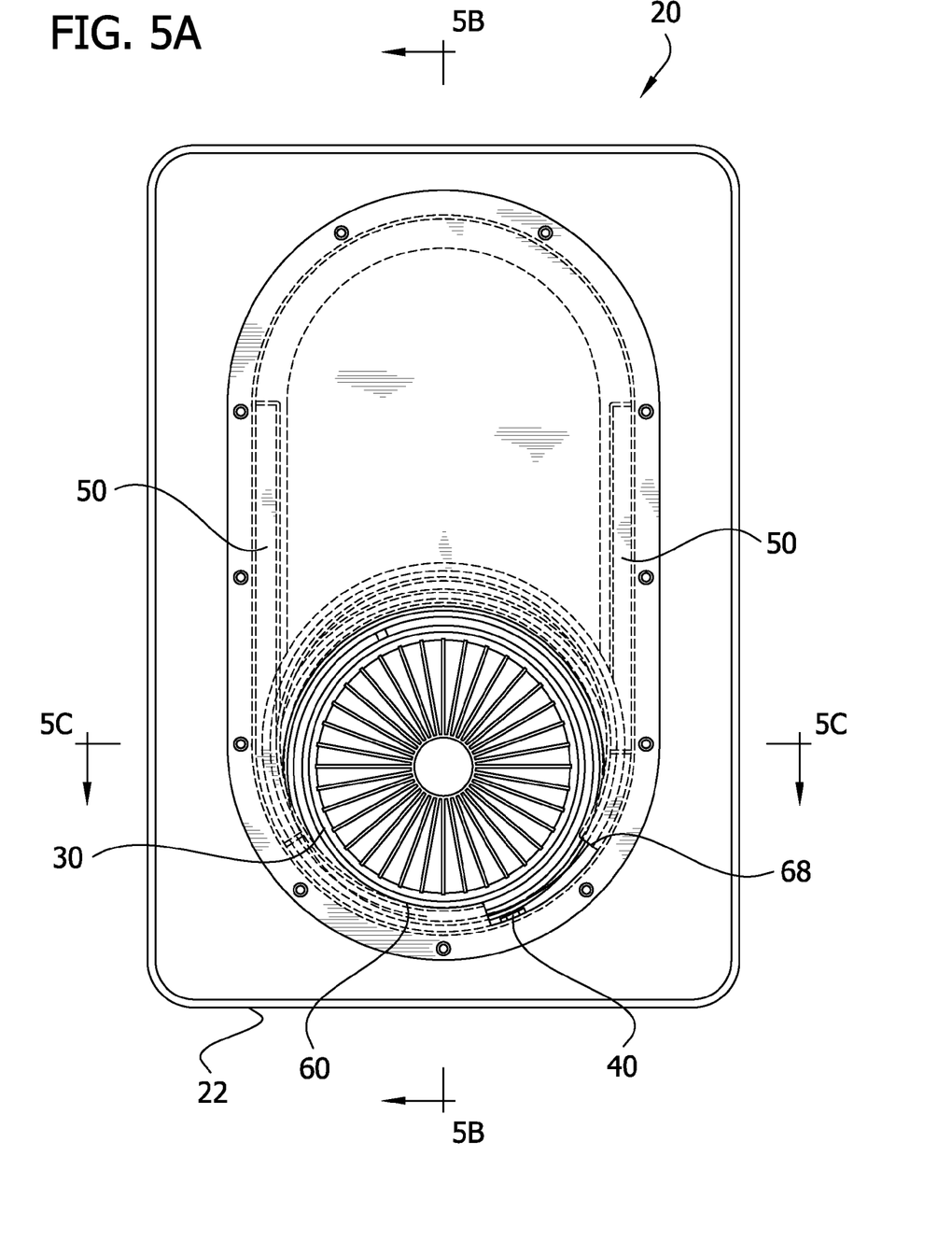
FIG. 5A is a top view of the lid with the closure in the locked position.
Figure 5B:
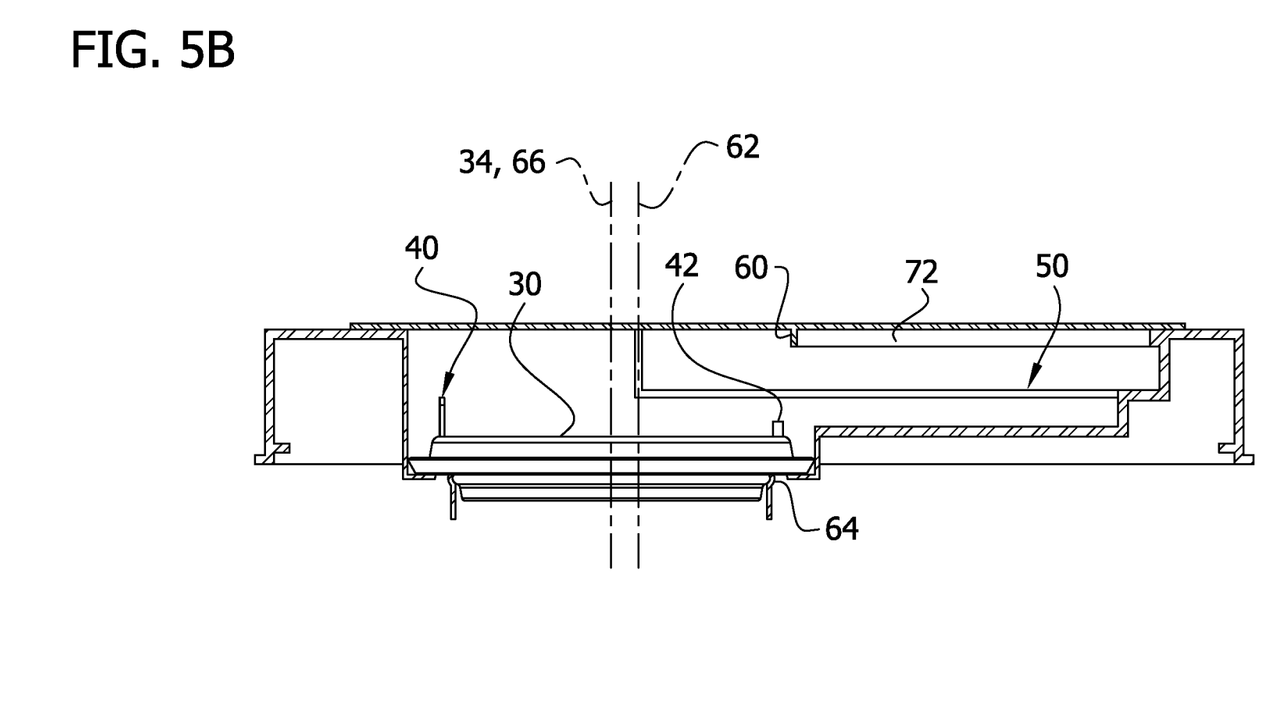
FIG. 5B is a vertical cross section of the lid of FIG. 5A taken in the plane 5B-5B.
Figure 5C:
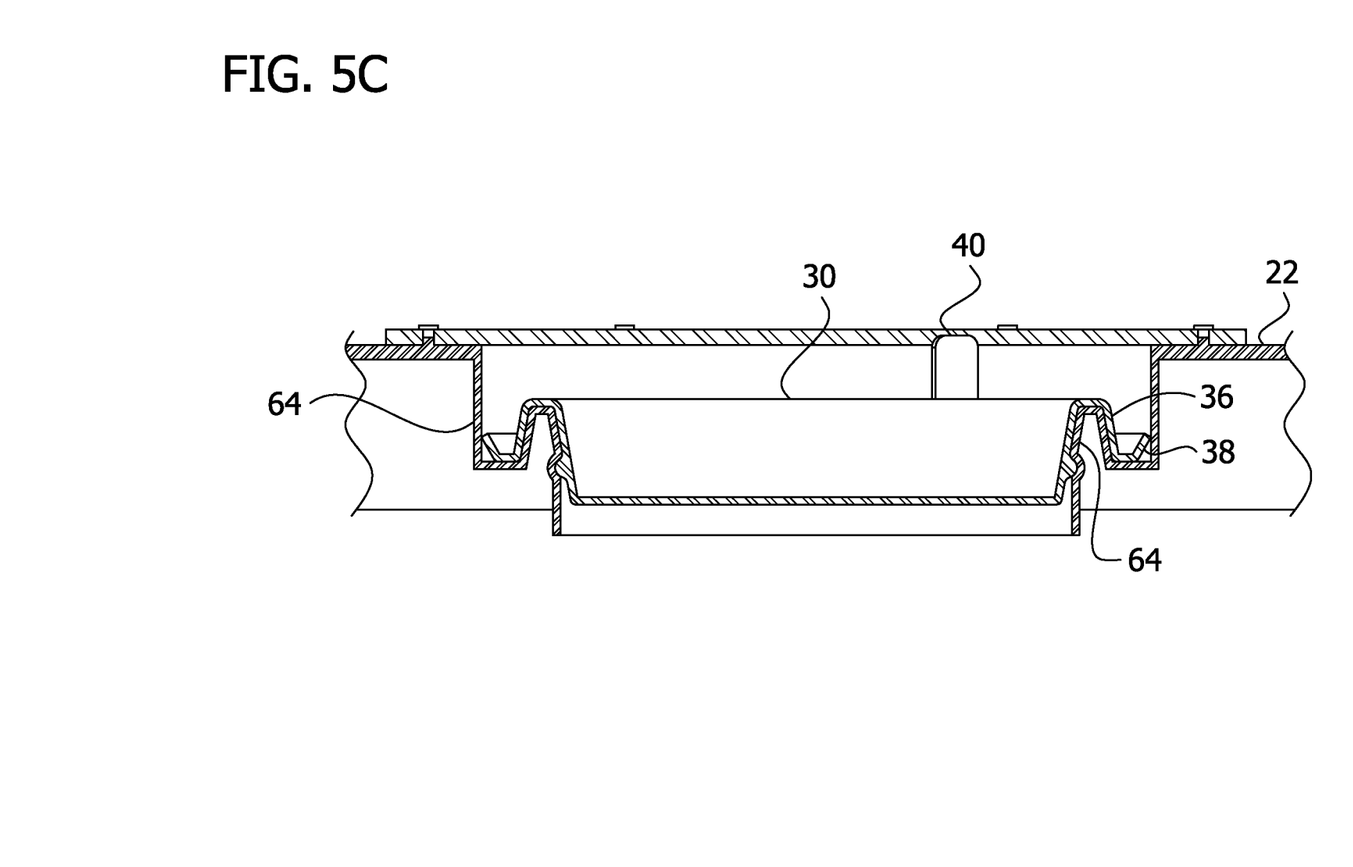
FIG. 5C is a horizontal cross section of the lid of FIG. 5B with portions cut away and taken in the plane 5C-5C.
Figure 5D:
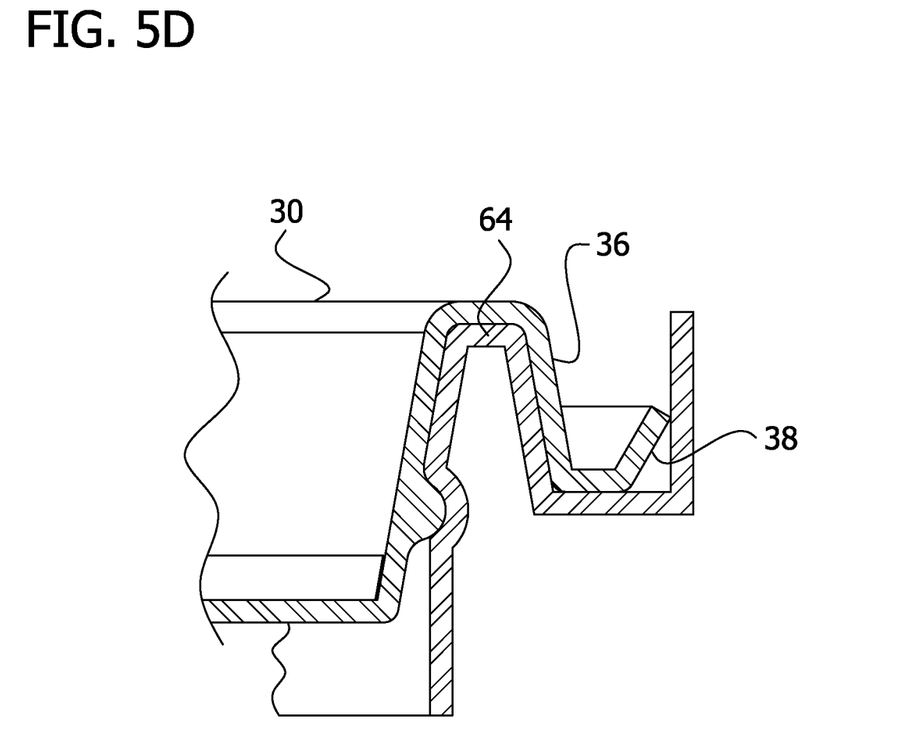
FIG. 5D is a magnified view of the cut-away portion of FIG. 5C to show detail.

As shown in FIGS. 2-4, the lid 20 also includes a closure 30 sized for selectively blocking the opening 26 in the cover 22. In one embodiment, both the opening 26 and the closure 30 are generally circular. The closure 30 includes a central portion 32 having a central axis 34, a peripheral flange 36 surrounding the central portion, and a resiliently compliant lip 38 extending from the flange. In one embodiment, the lip 38 extends away from the interior 14 of the medical waste receptacle base 12 when the cover 22 is covering the interior of the base. A protrusion 40 extends upward from the central portion 32 of the closure 30 adjacent the flange 36. The protrusion 40 is sized and shaped for gripping by a user to move the closure as will be explained in greater detail below. Thus, the protrusion 40 forms a handle extending away from the interior 14 of the medical waste receptacle base 12 when the cover 22 is covering the interior of the base. The closure 30 also includes a protuberance or boss 42 extending upward from a margin of the central portion 32 of the closure 30 adjacent the flange 36.

The closure 30 is operatively connected to the cover 22 for movement between an open position as shown in FIGS. 3A&B and a closed position as shown in FIGS. 4A-C. In the open position (FIGS. 3A&B), the closure 30 is at least partially out of alignment with the opening 26 in the cover 22 to allow medical waste W to pass through the opening to the interior 14 of the base 12. In the closed position (FIGS. 4A-C), the closure 30 is aligned with the opening 26 in the cover 22 to block the opening and to prevent medical waste W from passing through the opening to the interior 14 of the base 12.

The lid 20 includes a pair of parallel carriers, generally designated by 50, extending along the cover 22 toward opposite sides of the opening 26. Each of the carriers 50 includes a rail 52 extending downward from the cover 22 to a flange 54 that extends inward from the rail toward the opening 26. The carriers 50 receive the closure 30 between them so the peripheral flange 36 of the closure rests on the flanges 54 of the carriers. The lip 38 engages the rails 52 to center the closure 30 between the rails to center the closure and guide it into alignment with the opening 26. As will be appreciated by those skilled in the art, dimensions and positioning of the lip 38 may be altered to change a centering force provided by the lip.

As illustrated in FIGS. 3 & 4, the opening 26 is surrounded by a generally circular upper rim 60 surrounding an upper central axis 62 and a generally circular lower rim 64 surrounding a lower central axis 66. Although the upper rim 60 and lower rim 64 have a similar sizes and shapes, the upper and lower central axes 62, 66, respectively, are non-co-linear so the rims are laterally offset with respect to each other. In one embodiment, the upper and lower central axes 62, 66, respectively, are parallel, being offset by a distance of about 3/16 to about 1/8 inch. The upper rim 60 includes a notch 68 sized and shaped for receiving the protrusion 40 when the closure 30 is rotated from the closed position toward a locked position as will be described in detail below. When the notch 68 receives the protrusion 40, the central axis 34 of the closure 30 slides into alignment with the lower rim central axis 66 so the closure can move downward toward the lower rim 64. Once the closure 30 is vertically aligned with the lower rim 64, it can be rotated and lowered from the closed position as shown in FIGS. 4A-C to a locked position as shown in FIGS. 5A-D. As the closure 30 rotates from the closed position to the locked position, the center axis 34 of the closure remains coincident with the lower central axis 66. The lower rim 64 may include a conventional ratchet (not shown) to prevent the closure 30 from rotating out of the locked position. Thus, once the closure 30 is moved to the locked position, the waste receptacle 10 is effectively sealed so it cannot be reopened. The protrusion 40 is located so it contacts the upper rim 60 of the opening 26 to prevent the closure 30 from moving from the closed position to the locked position unless the closure is rotated and advanced so the protrusion enters the notch 68. Thus, the protrusion 40 reduces the potential for the closure 30 to be inadvertently moved to the locked position. Although the lid 20 may be formed with a notch and protrusion having other dimensions and positions to alter the amount the closure 30 must be rotated and advanced to engage the protrusion 40 with the notch 68, in one embodiment the notch and protrusion have dimensions and positions such that the closure must be rotated through an angle of about 5° to about 10° and advanced through a distance of about 3/16 to about 1/4 inch to engage the protrusion with the notch.

Figure 6:
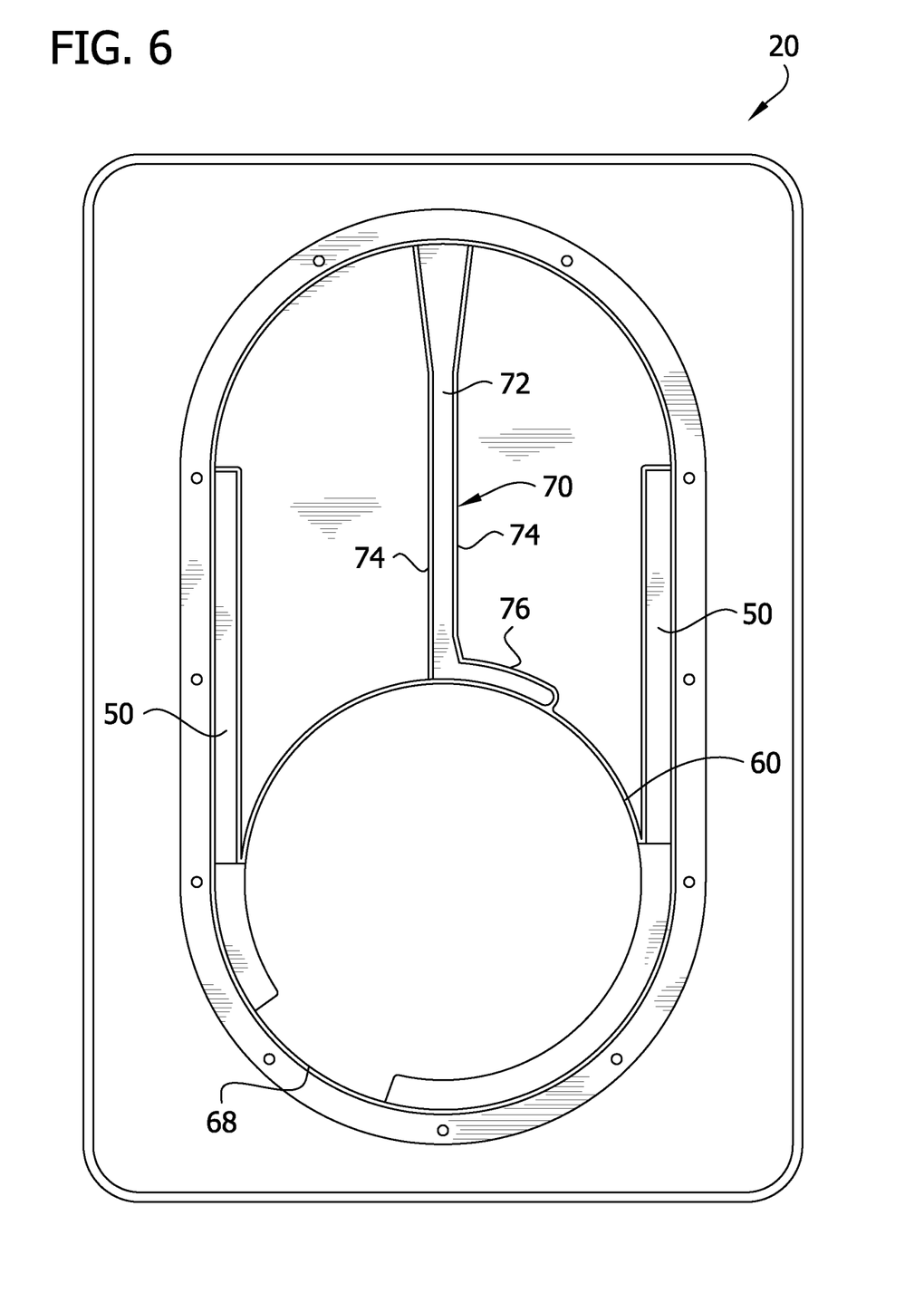
FIG. 6 is bottom view of the lid of the present invention; without the closure to show detail.

As illustrated in FIG. 6, the lid 20 also includes a guide, generally designated by 70, extending along the cover 22 for guiding the closure 30 between an open position as shown in FIGS. 3A&B, in which the closure is at least partially out of alignment with the opening 26 to allow medical waste W to pass through the opening for receipt in the interior 14 of the base 12, and a closed position as shown in FIGS. 4A-C, in which the center axis 34 of the closure is aligned with the upper rim central axis 62 to block the opening to prevent medical waste from passing through the opening. Although the guide 70 may take other shapes without departing from the scope of the present invention, in one embodiment the guide comprises a channel 72 formed between parallel rails 74 extending in a straight line along the closure 14. The rails 74 are spaced so the channel 72 has a width sized for receiving the protuberance 42. Thus, the channel 72 guides the closure 30 to move in a straight line between the open position and the closed position. The channel 72 also includes a lateral extension 76 that guides the protuberance 42 as the closure 30 moves from the closed position to the locked position. The lateral extension 76 permits the center axis 34 of the closure 30 to move into alignment with the lower rim central axis 66 allowing the closure to move to the locked position.

Although components of the present invention may be made of other materials without departing from the scope of the present invention, in one embodiment are formed from suitable plastics, such as polypropylene, polyethylene, and combinations thereof. The base and lid may be formed from any material that may provide suitable leak or puncture resistance and may be partially or completely transparent or translucent to monitor the level of medical waste. The components may be colored in conformance with industry standards. Because methods of making and assembling the components described above are conventional and well understood by those skilled in the art, they will not be described in this application.

To use the waste receptacle 10 of the present invention, a user drops medical waste W through the opening 26 in the cover 32. The medical waste W is stored in the base 12. Between uses, the opening 26 in the cover 32 of the receptacle 10 may be moved from the open position to the closed position to prevent contact with waste W stored in the base 12. To close the cover 32, the user grasps the protrusion 40 and slides the closure 30 toward the opening 26. As the closure 30 moves, the protuberance 42 slides along the channel 72 and the resiliently compliant lip 38 slides along the rails 52 of the guide 50. When the receptacle 10 is deemed to be at capacity, the user grasps the protrusion 40 and rotates and advances the closure 30 so the protrusion enters the notch 68. As the same time, the protuberance 42 slides along the lateral extension 76 of the channel 72. When the notch 68 receives the protrusion 40, the central axis 34 of the closure 30 slides into alignment with the lower rim central axis 66 so the closure can move downward toward the lower rim 64. Once the closure 30 is vertically aligned with the lower rim 64, it can be rotated from the closed position to the locked position and the receptacle 10 can be discarded according to industry practice.

In view of the above, it will be seen that the several objects of the invention are achieved and other advantageous results attained. A lid of a medical waste receptacle is provided that prevents accidental locking and provides automatic closure alignment.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A lid for covering an interior of a medical waste receptacle base, said lid comprising:
   a cover sized and shaped for covering the interior of the medical waste receptacle base, the cover having an opening sized for passing medical waste into the interior of the base;
   a pair of parallel carriers extending toward opposite sides of the opening, each of said parallel carriers comprising a vertical rail and a carrier flange extending from the vertical rail; and
   a closure sized and shaped for blocking the opening, said closure having a central portion, a peripheral flange surrounding the central portion, and a resiliently compliant lip extending from the flange and away from the interior of the medical waste receptacle base when the cover is covering the interior of the base, said lip engaging the vertical rail of each carrier to center the closure between the carriers for guiding the closure into alignment with the opening, the peripheral flange of the closure being positioned to engage the carrier flange of each carrier when the lip engages the vertical rail of each carrier.

2. A lid as set forth in claim 1, wherein each of said carrier flanges extend from the vertical rail at an angle.

3. A lid as set forth in claim 2, wherein each of said carrier flanges is generally horizontal.

4. A lid as set forth in claim 1, wherein said resiliently compliant lip extends around substantially all of the closure.

5. A lid as set forth in claim 1, wherein said resiliently compliant lip is non-parallel to said peripheral flange.

6. A lid as set forth in claim 1 wherein:
   the cover opening comprises a generally circular opening including a generally circular upper rim surrounding an upper central axis and a generally circular lower rim surrounding a lower central axis that is non-co-linear with said upper central axis; and
   the closure comprises a generally circular closure.

7. A lid as set forth in claim 6 further comprising a guide extending along the cover for guiding the closure along a straight line between an open position, in which the closure is at least partially out of alignment with the opening to allow medical waste to pass through the opening for receipt in the interior of the base, and a closed position, in which a center axis of the closure is aligned with the upper rim central axis to block the opening to prevent medical waste from passing through the opening, the closure being moveable from the closed position to a locked position in which the center axis of the closure is coincident with the lower rim central axis.

8. A lid as set forth in claim 7 further comprising a protrusion extending from the closure, the protrusion being located to contact the upper rim of the opening to prevent the closure from moving from the closed position to the locked position, and wherein the upper rim of the opening includes a notch for receiving the protrusion when the closure is rotated from the closed position, permitting the center axis of the closure to move into alignment with the lower rim central axis, thereby permitting the closure to move to the locked position.

9. A lid as set forth in claim 7 further comprising a protuberance extending from the closure, and wherein the guide comprises a channel sized for receiving the protuberance to guide the closure between the open position and the closed position and having a lateral extension for guiding the protuberance when the closure is in the closed position permitting the center axis of the closure to move into alignment with the lower rim central axis thereby allowing the closure to move to the locked position.

10. A medical waste receptacle comprising:
    a base having an interior sized and shaped for receiving medical waste;
    a cover sized and shaped for covering the interior of the medical waste receptacle base, the cover having an opening sized for passing medical waste into the interior of the base;
    a pair of parallel carriers extending toward opposite sides of the opening; and
    a closure sized and shaped for blocking the opening, said closure having a central portion, a peripheral flange surrounding the central portion, and a resiliently compliant lip extending from the flange and away from the interior of the medical waste receptacle base when the cover is covering the interior of the base, said lip extending around substantially all of said closure and engaging the carriers to center the closure between the carriers for guiding the closure into alignment with the opening.

11. A waste receptacle as set forth in claim 10, wherein each of said parallel carriers comprises a vertical rail and a carrier flange extending from the vertical rail at an angle, the lip engaging the vertical rail of each carrier and the peripheral flange of the closure engaging the carrier flange of each carrier.

12. A waste receptacle as set forth in claim 11, wherein each of said carrier flanges is generally horizontal.

13. A waste receptacle as set forth in claim 10, wherein said resiliently compliant lip is non-parallel to said peripheral flange.

14. A waste receptacle as set forth in claim 10 wherein:
the cover opening comprises a generally circular opening including a generally circular upper rim surrounding an upper central axis and a generally circular lower rim surrounding a lower central axis that is non-co-linear with said upper central axis; and
the closure comprises a generally circular closure.

15. A waste receptacle as set forth in claim 14 further comprising a guide extending along the cover for guiding the closure along a straight line between an open position, in which the closure is at least partially out of alignment with the opening to allow medical waste to pass through the opening for receipt in the interior of the base, and a closed position, in which a center axis of the closure is aligned with the upper rim central axis to block the opening to prevent medical waste from passing through the opening, the closure being moveable from the closed position to a locked position in which the center axis of the closure is coincident with the lower rim central axis.

16. A waste receptacle as set forth in claim 15 further comprising a protrusion extending from the closure, the protrusion being located to contact the upper rim of the opening to prevent the closure from moving from the closed position to the locked position, and wherein the upper rim of the opening includes a notch for receiving the protrusion when the closure is rotated from the closed position, permitting the center axis of the closure to move into alignment with the lower rim central axis, thereby permitting the closure to move to the locked position.

17. A waste receptacle as set forth in claim 15 further comprising a protuberance extending from the closure, and wherein the guide comprises a channel sized for receiving the protuberance to guide the closure between the open position and the closed position and having a lateral extension for guiding the protuberance when the closure is in the closed position permitting the center axis of the closure to move into alignment with the lower rim central axis thereby allowing the closure to move to the locked position.

18. A lid for covering an interior of a medical waste receptacle base, said lid comprising:
a cover sized and shaped for covering the interior of the medical waste receptacle base, the cover having an opening sized for passing medical waste into the interior of the base;
a pair of parallel carriers extending toward opposite sides of the opening; and
a closure sized and shaped for blocking the opening, said closure having a central portion, a peripheral flange surrounding the central portion, and a resiliently compliant lip extending at a non-zero angle from the flange and away from the interior of the medical waste receptacle base when the cover is covering the interior of the base, said lip engaging the carriers to center the closure between the carriers for guiding the closure into alignment with the opening.

19. A waste receptacle as set forth in claim 18, wherein each of said parallel carriers comprises a vertical rail and a carrier flange extending from the vertical rail at an angle, the lip engaging the vertical rail of each carrier and the peripheral flange of the closure engaging the carrier flange of each carrier.

20. A waste receptacle as set forth in claim 19, wherein each of said carrier flanges is generally horizontal.

* * * * *